(12) United States Patent
Bonadio et al.

(10) Patent No.: US 7,537,564 B2
(45) Date of Patent: *May 26, 2009

(54) WOUND RETRACTOR DEVICE

(75) Inventors: Frank Bonadio, Bray (IE); Trevor Vaugh, Birr (IE); John Butler, Blackrock (IE)

(73) Assignee: Atropos Limited, County Wicklow (IE)

( * ) Notice: Subject to any disclaimer, the term of this patent is extended or adjusted under 35 U.S.C. 154(b) by 396 days.

This patent is subject to a terminal disclaimer.

(21) Appl. No.: 11/086,661

(22) Filed: Mar. 23, 2005

(65) Prior Publication Data

US 2005/0197537 A1 Sep. 8, 2005

Related U.S. Application Data

(63) Continuation-in-part of application No. 10/995,117, filed on Nov. 24, 2004, now Pat. No. 7,300,399, which is a continuation of application No. 10/133,979, filed on Apr. 29, 2002, now Pat. No. 6,846,287, which is a continuation of application No. 09/801,826, filed on Mar. 9, 2001, now abandoned, which is a continuation of application No. PCT/IE99/00122, filed on Dec. 1, 1999.

(60) Provisional application No. 60/555,398, filed on Mar. 23, 2004.

(30) Foreign Application Priority Data

Dec. 1, 1998 (IE) .................................... 980997
Feb. 15, 1999 (IE) .................................... 990111

(51) Int. Cl.
*A61B 1/267* (2006.01)
(52) U.S. Cl. ...................................... 600/208
(58) Field of Classification Search ................. 600/208, 600/213, 226
See application file for complete search history.

(56) References Cited

U.S. PATENT DOCUMENTS 1,157,202 A 10/1915 McLeland (Continued)

FOREIGN PATENT DOCUMENTS

DE 37 39 532 12/1988

OTHER PUBLICATIONS

International Search Report in PCT/IE2005/000029 mailed on Jun. 17, 2005.

*Primary Examiner*—Cris L Rodriguez
*Assistant Examiner*—Rachel A Running
(74) *Attorney, Agent, or Firm*—Finnegan, Henderson, Farabow, Garrett & Dunner LLP

(57) ABSTRACT

A wound retractor device (1) comprises a distal ring member (2) for insertion into a wound opening (3), a proximal ring member (4) for location externally of the wound opening (3), and four strap members (5) extending between the proximal ring member (4) and the distal ring member (2). The four separate strap members (5) are axially movable relative to the distal ring member (2) and relative to the proximal ring member (4). The distal ring member (2) comprises four slots (6), with each strap member (5) positioned extending through a slot (6). The slots (6) thus act as passageways through which the strap members (5) may extend, and in this manner the slots (6) guide movement of the strap members (5) relative to the distal ring member (2). The proximal ring member (4) also comprises four slots (7) which act as passageways to guide movement of the strap members (5) relative to the proximal ring member (4). In use, the distal ring member (2) is inserted into the wound opening (3), and the proximal ring member (4) is located externally of the wound opening (3). The second end (10) of each strap member (5) is then gripped, and a pulling force is exerted to retract laterally the sides of the wound opening (3).

29 Claims, 14 Drawing Sheets

U.S. PATENT DOCUMENTS

| | | | |
|---|---|---|---|
| 1,598,284 A | 8/1926 | Kinney | |
| 1,810,466 A | 6/1931 | Deutsch | |
| 2,219,564 A | 10/1940 | Reyniers | |
| 2,305,289 A | 12/1942 | Coburg | |
| 2,695,608 A | 11/1954 | Gibbon | |
| 2,835,253 A | 5/1958 | Borgeson | |
| 3,111,943 A | 11/1963 | Orndorff | |
| 3,244,169 A | 4/1966 | Baxter | |
| 3,332,417 A | 7/1967 | Blanford et al. | |
| 3,347,226 A | 10/1967 | Harrower | |
| 3,347,227 A | 10/1967 | Harrower | |
| 3,397,692 A | 8/1968 | Creager, Jr. et al. | |
| 3,522,800 A | 8/1970 | Lesser | |
| 3,523,534 A | 8/1970 | Nolan | |
| 3,570,475 A | 3/1971 | Weinstein | |
| 3,592,198 A * | 7/1971 | Evans | 606/124 |
| 3,729,006 A | 4/1973 | Wilder et al. | |
| 3,782,370 A | 1/1974 | McDonald | |
| 3,797,478 A | 3/1974 | Walsh et al. | |
| 3,807,393 A | 4/1974 | McDonald | |
| 3,841,332 A | 10/1974 | Treacle | |
| 3,907,389 A | 9/1975 | Cox et al. | |
| 3,915,171 A | 10/1975 | Shermeta | |
| 3,965,890 A | 6/1976 | Gauthier | |
| 3,998,217 A | 12/1976 | Trumbull et al. | |
| 4,024,872 A | 5/1977 | Muldoon | |
| 4,030,500 A | 6/1977 | Ronnquist | |
| 4,096,853 A | 6/1978 | Weigand | |
| 4,130,113 A | 12/1978 | Graham | |
| 4,188,945 A | 2/1980 | Wenander | |
| 4,228,792 A | 10/1980 | Rhys-Davies | |
| 4,239,036 A | 12/1980 | Krieger | |
| 4,367,728 A | 1/1983 | Mutke | |
| 4,399,816 A | 8/1983 | Spangler | |
| 4,434,791 A | 3/1984 | Darnell | |
| 4,485,490 A | 12/1984 | Akers et al. | |
| 4,550,713 A | 11/1985 | Hyman | |
| 4,553,537 A | 11/1985 | Rosenberg | |
| 4,601,710 A | 7/1986 | Moll | |
| 4,654,030 A | 3/1987 | Moll et al. | |
| 4,777,943 A | 10/1988 | Chvapil | |
| 4,889,107 A | 12/1989 | Kaufman | |
| 4,895,565 A | 1/1990 | Hillstead | |
| 4,903,710 A | 2/1990 | Jessamine et al. | |
| 4,950,222 A | 8/1990 | Scott et al. | |
| 4,984,564 A | 1/1991 | Yuen | |
| 4,991,593 A | 2/1991 | LeVahn | |
| 4,998,538 A | 3/1991 | Charowsky et al. | |
| 5,041,095 A | 8/1991 | Littrell | |
| 5,045,070 A | 9/1991 | Grodecki et al. | |
| D320,658 S | 10/1991 | Quigley et al. | |
| 5,125,897 A | 6/1992 | Quinn et al. | |
| 5,158,553 A | 10/1992 | Berry et al. | |
| 5,159,921 A | 11/1992 | Hoover | |
| 5,161,773 A | 11/1992 | Tower | |
| 5,178,162 A | 1/1993 | Bose | |
| 5,188,595 A | 2/1993 | Jacobi | |
| 5,211,370 A | 5/1993 | Powers | |
| 5,213,114 A | 5/1993 | Bailey, Jr. | |
| 5,234,455 A | 8/1993 | Mulhollan | |
| 5,248,304 A | 9/1993 | Vigdorchik et al. | |
| 5,263,922 A | 11/1993 | Sova et al. | |
| D343,236 S | 1/1994 | Quigley et al. | |
| D346,022 S | 4/1994 | Quigley et al. | |
| 5,299,582 A | 4/1994 | Potts | |
| 5,309,896 A | 5/1994 | Moll et al. | |
| 5,316,541 A | 5/1994 | Fischer | |
| 5,342,385 A | 8/1994 | Norelli et al. | |
| 5,350,364 A | 9/1994 | Stephens et al. | |
| 5,364,345 A | 11/1994 | Lowery et al. | |
| 5,366,478 A | 11/1994 | Brinkerhoff et al. | |
| 5,368,545 A | 11/1994 | Schaller et al. | |
| 5,391,156 A | 2/1995 | Hildwein et al. | |
| 5,429,609 A | 7/1995 | Yoon | |
| 5,480,410 A | 1/1996 | Cuschieri et al. | |
| 5,514,133 A | 5/1996 | Golub et al. | |
| 5,522,791 A | 6/1996 | Leyva | |
| 5,524,644 A | 6/1996 | Crook | |
| 5,526,536 A | 6/1996 | Cartmill | |
| 5,545,179 A | 8/1996 | Williamson, IV | |
| 5,634,911 A | 6/1997 | Hermann et al. | |
| 5,634,937 A | 6/1997 | Mollenauer et al. | |
| 5,636,645 A | 6/1997 | Ou | |
| 5,640,977 A | 6/1997 | Leahy et al. | |
| 5,649,550 A | 7/1997 | Crook | |
| 5,653,705 A | 8/1997 | de la Torre et al. | |
| 5,672,168 A | 9/1997 | de la Torre et al. | |
| 5,707,703 A | 1/1998 | Rothrum et al. | |
| 5,741,234 A | 4/1998 | Aboul-Hosn | |
| 5,741,298 A | 4/1998 | MacLeod | |
| 5,755,660 A | 5/1998 | Tyagi | |
| 5,769,783 A | 6/1998 | Fowler | |
| 5,803,921 A | 9/1998 | Bonadio | |
| 5,810,721 A | 9/1998 | Mueller et al. | |
| 5,813,409 A | 9/1998 | Leahy et al. | |
| 5,832,925 A | 11/1998 | Rothrum | |
| 5,853,395 A | 12/1998 | Crook et al. | |
| 5,899,208 A | 5/1999 | Bonadio | |
| 5,906,577 A | 5/1999 | Beane et al. | |
| 5,947,922 A | 9/1999 | MacLeod | |
| 5,951,467 A | 9/1999 | Picha et al. | |
| 5,957,913 A | 9/1999 | de la Torre et al. | |
| 5,964,781 A | 10/1999 | Mollenauer et al. | |
| 5,997,515 A | 12/1999 | de la Torre et al. | |
| 6,033,426 A | 3/2000 | Kaji | |
| 6,033,428 A | 3/2000 | Sardella | |
| 6,042,573 A | 3/2000 | Lucey | |
| 6,048,309 A | 4/2000 | Flom et al. | |
| 6,077,288 A | 6/2000 | Shimomura et al. | |
| 6,110,154 A | 8/2000 | Shimomura et al. | |
| 6,142,935 A | 11/2000 | Flom et al. | |
| 6,142,936 A | 11/2000 | Beane et al. | |
| 6,163,949 A | 12/2000 | Neuenschwander | |
| 6,164,279 A | 12/2000 | Tweedle | |
| 6,171,282 B1 | 1/2001 | Ragsdale | |
| 6,183,486 B1 | 2/2001 | Snow et al. | |
| 6,254,533 B1 | 7/2001 | Fadem et al. | |
| 6,254,534 B1 | 7/2001 | Butler et al. | |
| 6,319,246 B1 | 11/2001 | de la Torre et al. | |
| 6,346,074 B1 | 2/2002 | Roth | |
| 6,382,211 B1 | 5/2002 | Crook | |
| 6,450,983 B1 | 9/2002 | Rambo | |
| 6,578,577 B2 | 6/2003 | Bonadio et al. | |
| 6,582,364 B2 | 6/2003 | Butler et al. | |
| 6,623,426 B2 | 9/2003 | Bonadio et al. | |
| 6,840,951 B2 | 1/2005 | de la Torre et al. | |
| 6,846,287 B2 | 1/2005 | Bonadio et al. | |
| 2005/0020884 A1 | 1/2005 | Heart et al. | |

FOREIGN PATENT DOCUMENTS

| | | |
|---|---|---|
| DE | 37 37 121 | 5/1989 |
| DE | 296 00 939 | 6/1998 |
| EP | 0142262 | 5/1985 |
| EP | 0537768 | 4/1993 |
| EP | 0950376 | 10/1999 |
| EP | 1118657 | 7/2001 |
| FR | 1456623 | 9/1996 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |

| | | | | | | |
|---|---|---|---|---|---|---|
| GB | 1496696 | 12/1977 | | WO | WO 97/32515 | 9/1997 |
| GB | 2071502 | 9/1981 | | WO | WO 98/35614 | 8/1998 |
| GB | 2255019 | 10/1992 | | WO | WO 98/48724 | 11/1998 |
| GB | 2275420 | 8/1994 | | WO | WO 99/03416 | 1/1999 |
| JP | 10-108868 | 4/1998 | | WO | WO 99/25268 | 5/1999 |
| JP | 2001-61850 | 3/2001 | | WO | WO 99/29250 | 6/1999 |
| JP | 2004-195037 | 7/2004 | | WO | WO 00/32116 | 6/2000 |
| RU | 1342485 | 1/1997 | | WO | WO 00/32117 | 6/2000 |
| WO | WO 86/06272 | 11/1986 | | WO | WO 00/32119 | 6/2000 |
| WO | WO 92/11880 | 7/1992 | | WO | WO 00/32120 | 6/2000 |
| WO | WO 92/21292 | 12/1992 | | WO | WO 00/35356 | 6/2000 |
| WO | WO 93/05740 | 4/1993 | | WO | WO 00/54675 | 9/2000 |
| WO | WO 95/05207 | 2/1995 | | WO | WO 00/54676 | 9/2000 |
| WO | WO 95/07056 | 3/1995 | | WO | WO 00/54677 | 9/2000 |
| WO | WO 95/22289 | 8/1995 | | WO | WO 01/08563 | 2/2001 |
| WO | WO 95/27445 | 10/1995 | | WO | WO 01/08581 | 2/2001 |
| WO | WO 95/27468 | 10/1995 | | WO | WO 01/26558 | 4/2001 |
| WO | WO 96/36283 | 11/1996 | | WO | WO 01/91652 | 12/2001 |
| WO | WO 97/32514 | 9/1997 | | WO | WO 02/34108 A2 | 5/2002 |
| | | | | WO | WO 03/034908 A3 | 5/2003 |
| | | | | WO | WO 03/061480 A1 | 7/2003 |
| | | | | WO | WO 03/103548 A1 | 12/2003 |

\* cited by examiner

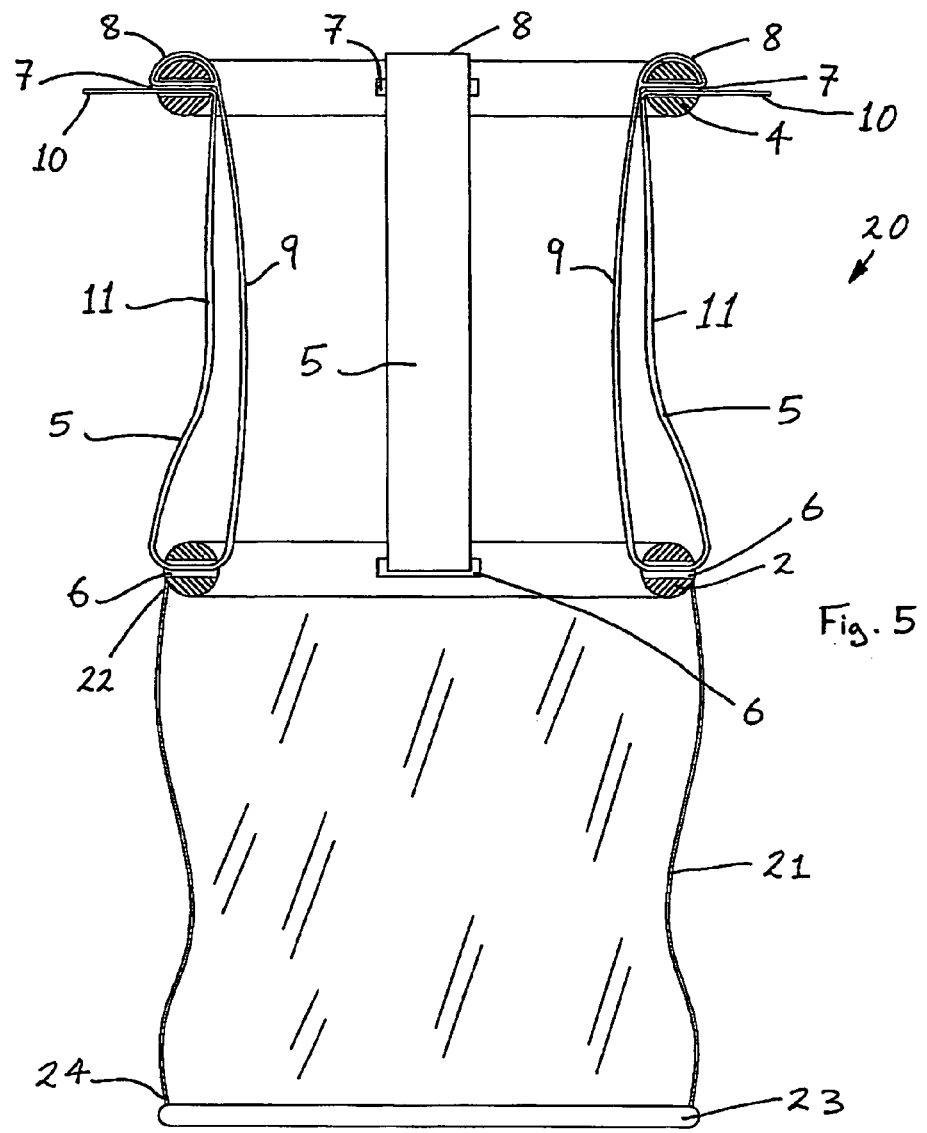
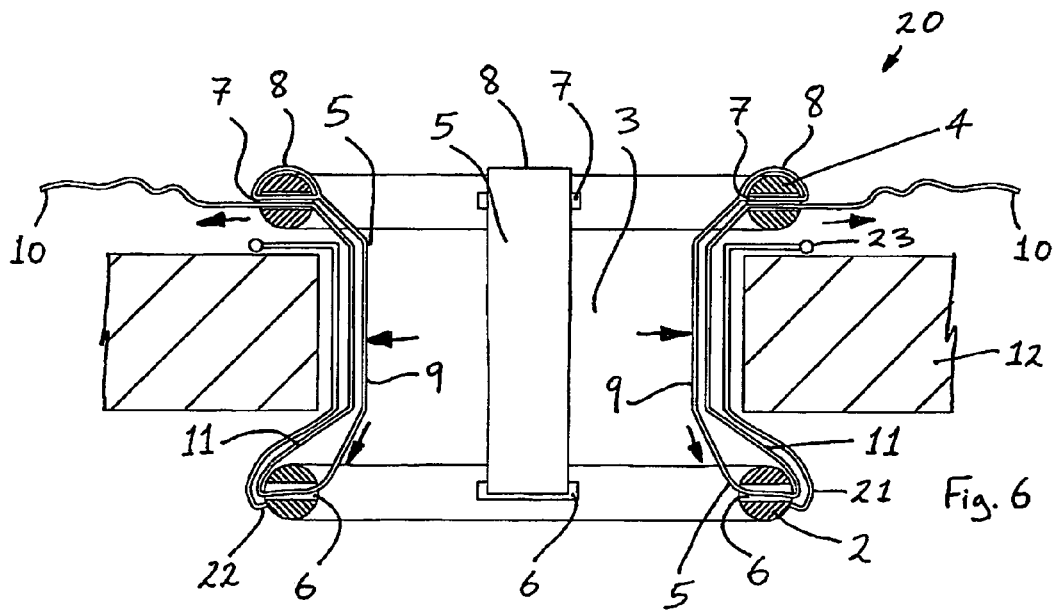

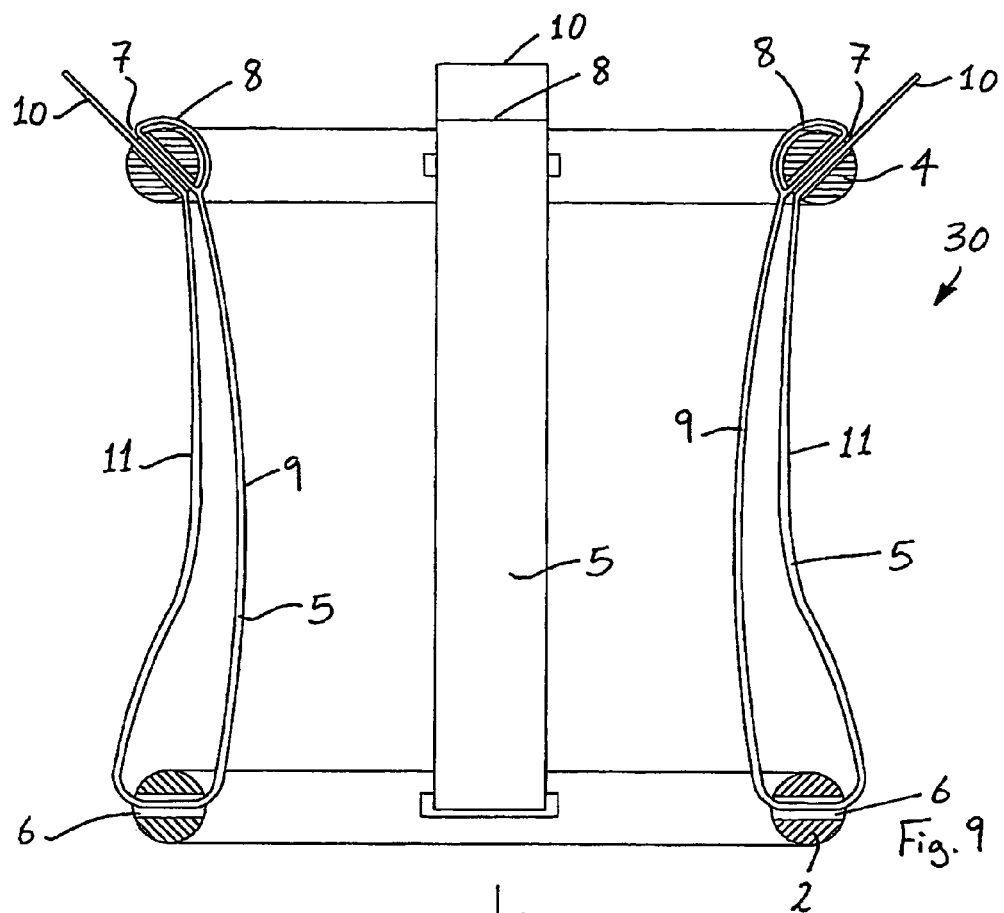
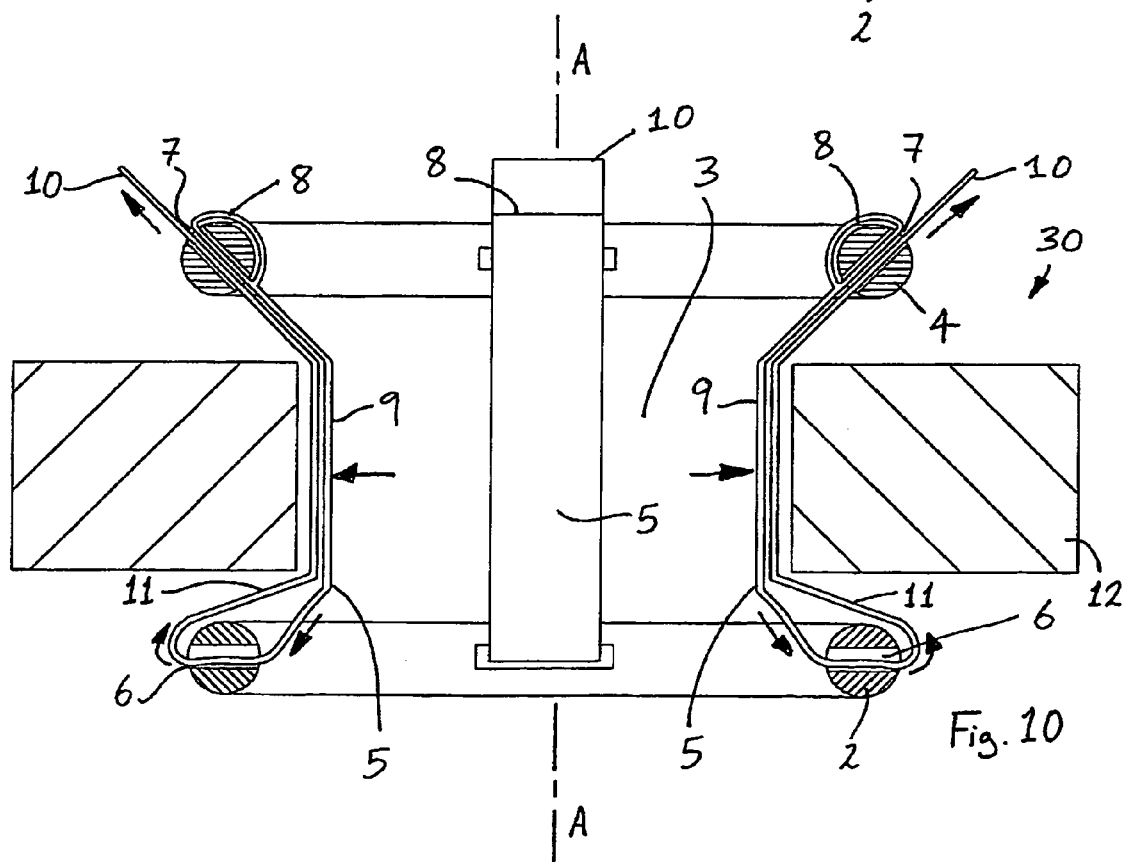

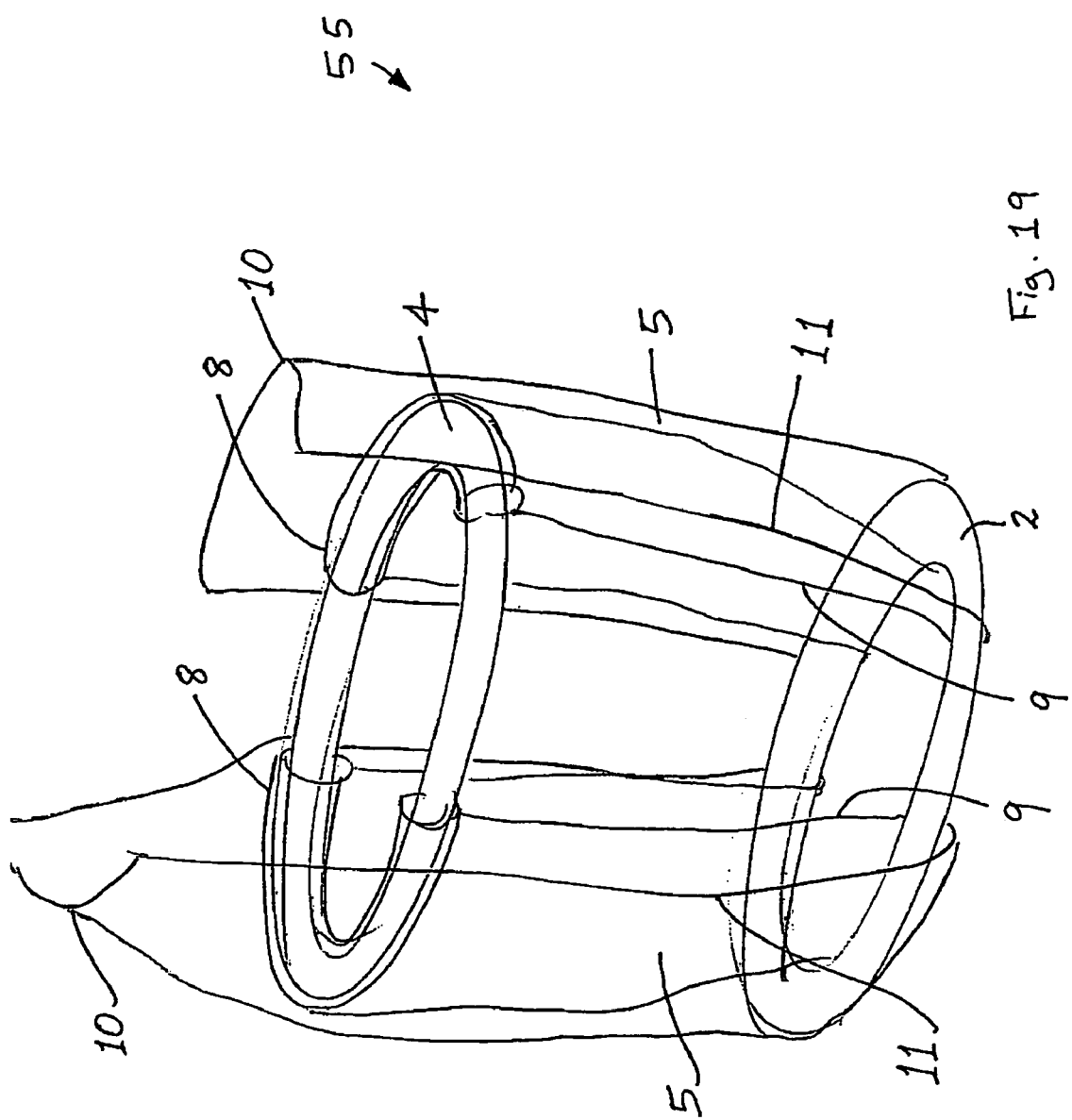

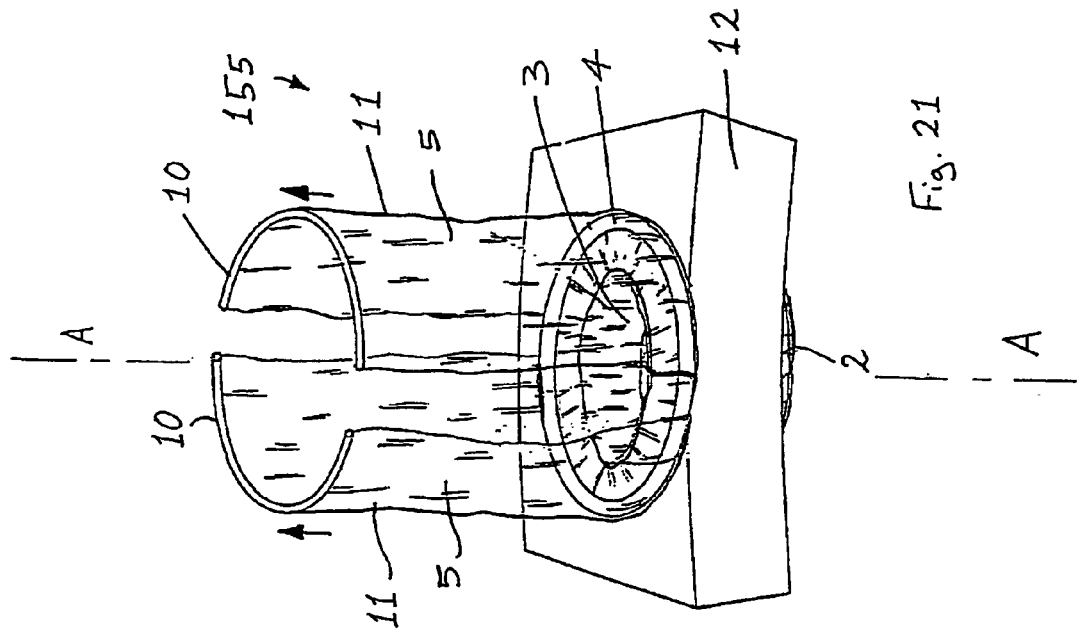
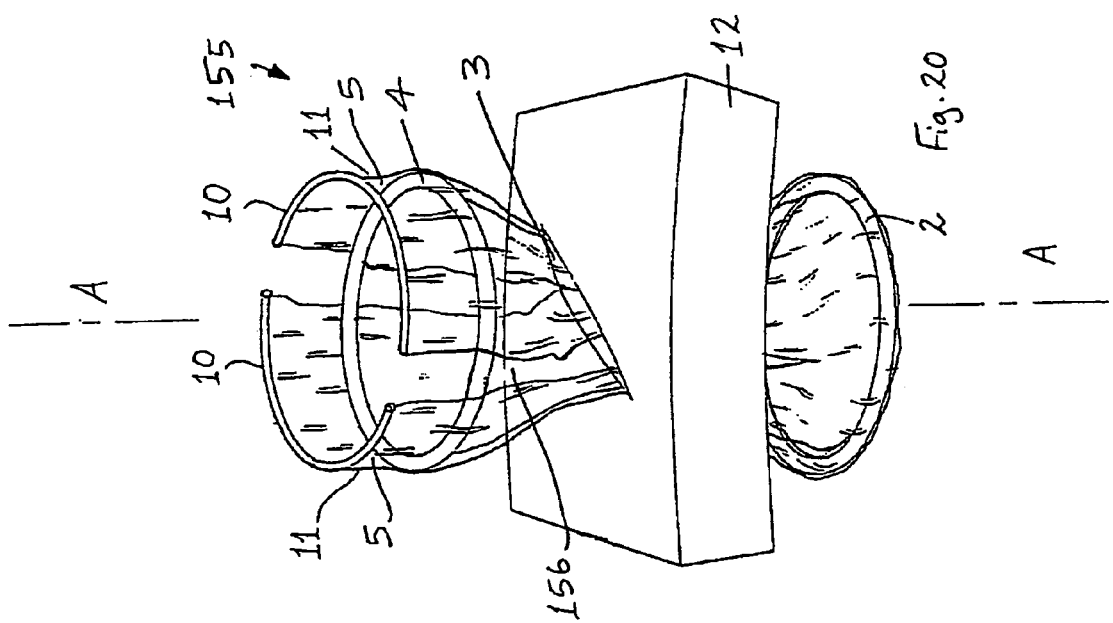

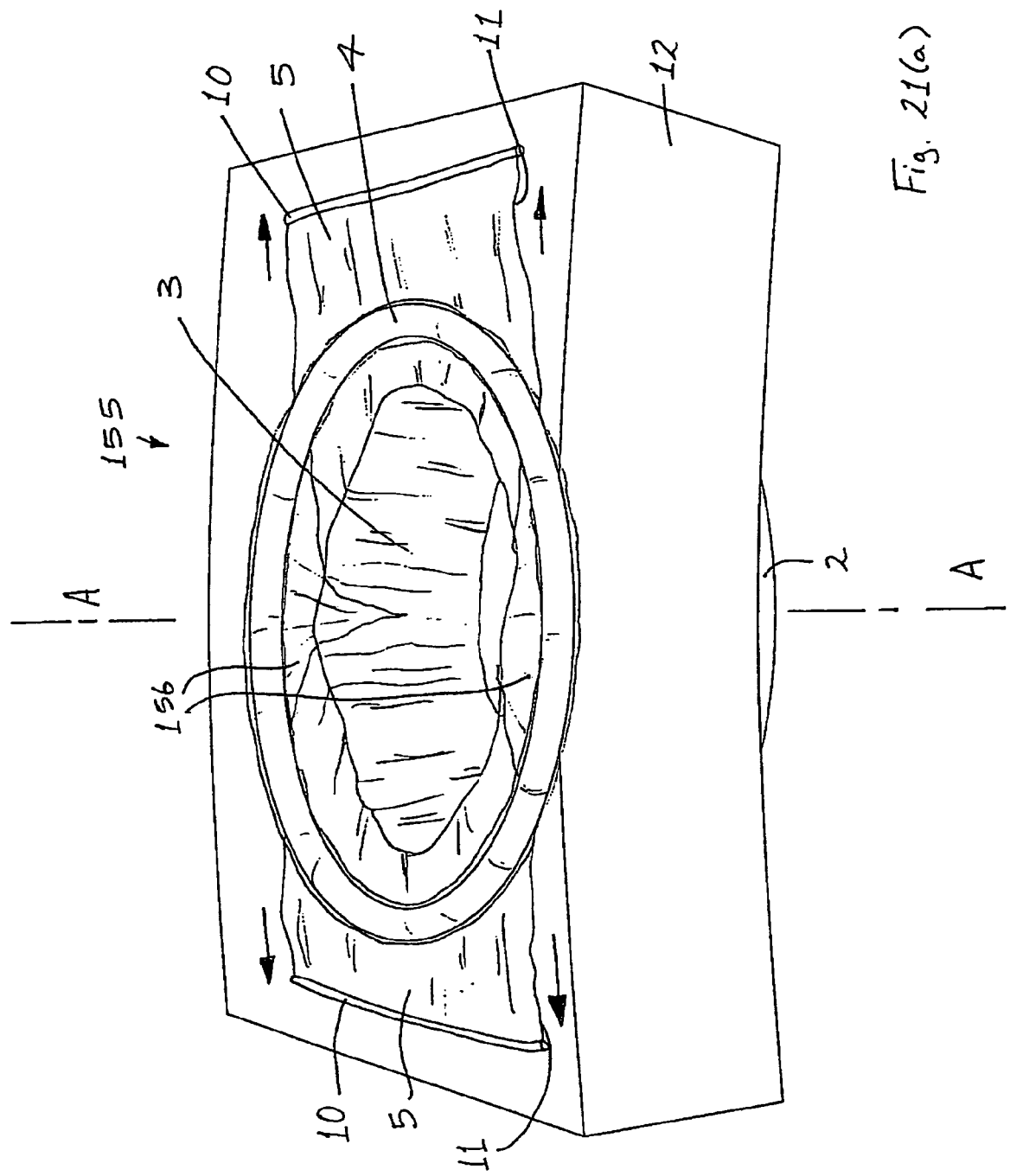

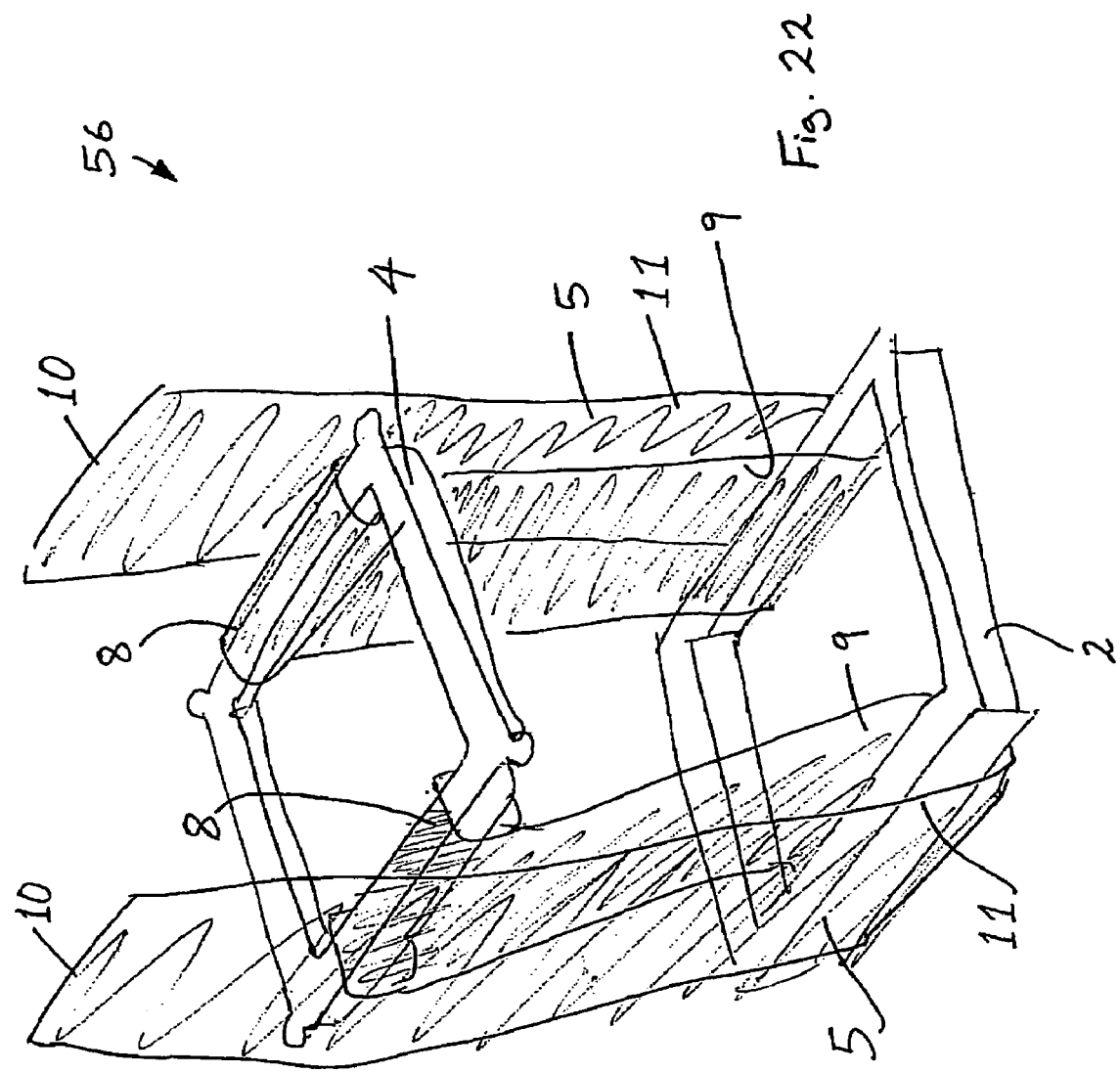

WOUND RETRACTOR DEVICE

This is a continuation-in-part of application Ser. No. 10/995,117, filed Nov. 24, 2004 now U.S. Pat. No. 7,300,399, which is a continuation of application Ser. No. 10/133,979, filed Apr. 29, 2002, now U.S. Pat. No. 6,846,287, which is a continuation of application Ser. No. 09/801,826, filed Mar. 9, 2001, now abandoned, which is a continuation of PCT International Application No. PCT/IE99/00122, filed Dec. 1, 1999. This application claims the benefit of U.S. Provisional Application No. 60/555,398, filed on Mar. 23, 2004. The contents of all of the above-listed applications are incorporated herein by reference.

INTRODUCTION

This invention relates to a wound retractor device, and to a method of retracting a wound opening.

STATEMENTS OF INVENTION

According to the invention there is provided a wound retractor device comprising:
- a distal member for insertion into a wound opening;
- a proximal member for location externally of the wound opening; and
- a connecting member extending at least between the distal member and the proximal member;
- at least part of the connecting member being movable relative to the proximal member to shorten the length of the connecting member located between the distal member and the proximal member and thereby retract laterally the sides of the wound opening.

In one embodiment of the invention the connecting member comprises at least one strap member. The connecting member may comprise two or more strap members. In one case a first strap member is separate from a second strap member. In another case a first strap member is attached to a second strap member.

The connecting member may comprise a sleeve member. The sleeve member may provide the means of attachment of the first strap member to the second strap member. In one case the first strap member extends from the sleeve member in a first direction, and the second strap member extends from the sleeve member in the first direction. The sum of the circumferential dimensions of the strap members may be substantially equal to the circumferential dimension of the sleeve member. The strap member may be attached to an end of the sleeve member. In one case the first strap member is attached to a first end of the sleeve member, and the second strap member is attached to the first end of the sleeve member.

In one case the connecting member is axially movable relative to the proximal member.

At least part of the connecting member may be movable relative to the proximal member in a lateral direction. In one case at least part of the connecting member is movable relative to the proximal member in a direction substantially perpendicular to a longitudinal axis of a wound opening. In another case at least part of the connecting member is movable relative to the proximal member in a direction substantially parallel to a longitudinal axis of a wound opening.

At least part of the connecting member may be slidably movable relative to the proximal member.

In one embodiment of the invention the device comprises a guide to guide movement of the connecting member relative to the proximal member. The guide may comprise a passageway through which the connecting member is extendable. The passageway may be provided by a slot in the proximal member. A longitudinal axis of the passageway may be substantially perpendicular to a longitudinal axis of a wound opening. A longitudinal axis of the passageway may be substantially parallel to a longitudinal axis of a wound opening.

In one case the connecting member is movable relative to the distal member. The device may comprise a guide to guide movement of the connecting member relative to the distal member. The guide may comprise a passageway through which the connecting member is extendable. In one case the passageway is provided by a slot in the distal member. A longitudinal axis of the passageway may be substantially perpendicular to a longitudinal axis of a wound opening. A longitudinal axis of the passageway may be substantially parallel to a longitudinal axis of a wound opening.

In one embodiment the connecting member extends between the distal member and the proximal member in a double layer. The connecting member may be looped around at least part of the distal member. In one case a first end of the connecting member is fixed relative to the proximal member. A second end of the connecting member may be movable relative to the proximal member. In one case the connecting member extends from the first end distally to the distal member in a first layer, and extends from the distal member proximally to the second end in a second layer, the second layer being radially outwardly of the first layer. In another case the connecting member extends from the first end distally to the distal member in a first layer, and extends from the distal member proximally to the second end in a second layer, the second layer being radially inwardly of the first layer.

In one case the device is configured to self-lock the connecting member in position relative to the proximal member.

In a further embodiment the connecting member is fixed relative to the distal member.

The connecting member may extend between the distal member and the proximal member in a single layer.

In one case at least part of the connecting member is grippable to move at least part of the connecting member relative to the proximal member. The grippable part of the connecting member may be configured to the located externally of a wound opening.

In a further embodiment the device comprises a lock to releasably lock the connecting member in position relative to the proximal member. The lock may comprise a male protrusion for co-operating engagement with a female recess.

In one case the proximal member comprises the male protrusion, and the connecting member comprises the female recess. The lock may comprise a plurality of female recesses.

In another case the lock comprises an engagement member releasably fixable to the connecting member to engage against the proximal member. The engagement member may comprise a clamp.

In another embodiment the device comprises a protector to protect a retracted wound opening. The protector may comprise a sleeve member to line a retracted wound opening. The sleeve member may be mounted to the distal member. In one case a first end of the sleeve member is fixed to the distal member and a second end of the sleeve member is configured for location externally of a wound opening.

The proximal member may comprise a ring. The distal member may comprise a ring. The ring may be substantially circular. The ring may be substantially square-shaped.

In one embodiment the connecting member comprises a plurality of strap members spaced around the circumference of the proximal member and/or the distal member.

In another aspect of the invention there is provided a method of retracting a wound opening, the method comprising the steps of:

providing a wound retractor device comprising a distal member, a proximal member, and a connecting member extending at least between the distal member and the proximal member;

inserting the distal member into the wound opening, and locating the proximal member externally of the wound opening; and moving at least part of the connecting member relative to the proximal member to shorten the length of the connecting member located between the distal member and the proximal member and thereby retract laterally the sides of the wound opening.

In one case at least part of the connecting member is moved relative to the proximal member in a lateral direction. At least part of the connecting member may be moved relative to the proximal member in a direction substantially perpendicular to a longitudinal axis of the wound opening.

In another case at least part of the connecting member is moved relative to the proximal member in a direction substantially parallel to a longitudinal axis of the wound opening. At least part of the connecting member may be slidably moved relative to the proximal member.

The method may comprise the steps of gripping at least part of the connecting member and exerting a force on the connecting member to move at least part of the connecting member relative to the proximal member. In one case the method comprises the step of releasing the connecting member after lateral retraction of the sides of the wound opening.

In one embodiment the method comprises the step of guiding movement of the connecting member relative to the proximal member.

In another case the method comprises the step of moving the connecting member relative to the distal member. The method may comprise the step of guiding movement of the connecting member relative the distal member.

In one case the connecting member is locked in position relative to the proximal member after lateral retraction of the sides of the wound opening. In one case the wound retractor device self-locks the connecting member in position relative to the proximal member.

In another case the method comprises the step of releasably locking the connecting member in position relative to the proximal member. The connecting member may be releasably locked in position relative to the proximal member by engaging a male protrusion with a female recess. The connecting member may be releasably locked in position relative to the proximal member by fixing an engagement member to the connecting member, and engaging the engagement member against the proximal member.

The method may comprise the step of protecting the retracted wound opening. The method may comprise the step of locating a protector between the connecting member and the sides of the wound opening. In one case step of locating the protector between the connecting member and the sides of the wound opening is performed after the distal member is inserted into the wound opening. In one case the protector is inserted into the wound opening with the distal member. The protector may be retrieved from within the wound opening to locate the protector between the connecting member and the sides of the wound opening.

BRIEF DESCRIPTION OF THE DRAWINGS

The invention will be more clearly understood from the following description of some embodiments thereof, given by way of example only, with reference to the accompanying drawings, in which:

FIGS. 4 to 6 are views similar to FIGS. 1 to 3 of another wound retractor device according to the invention;

FIGS. 9 and 10 are views similar to FIGS. 2 and 3 of another wound retractor device according to the invention;

FIG. 19 is a perspective view of another wound retractor device according to the invention;

FIGS. 20 and 21 are perspective views of another wound retractor device according to the invention, in use;

FIG. 21(a) is another perspective view of the device of FIG. 20, in use; and

FIG. 22 is a perspective view of a further wound retractor device according to the invention.

DETAILED DESCRIPTION

Figure 1:
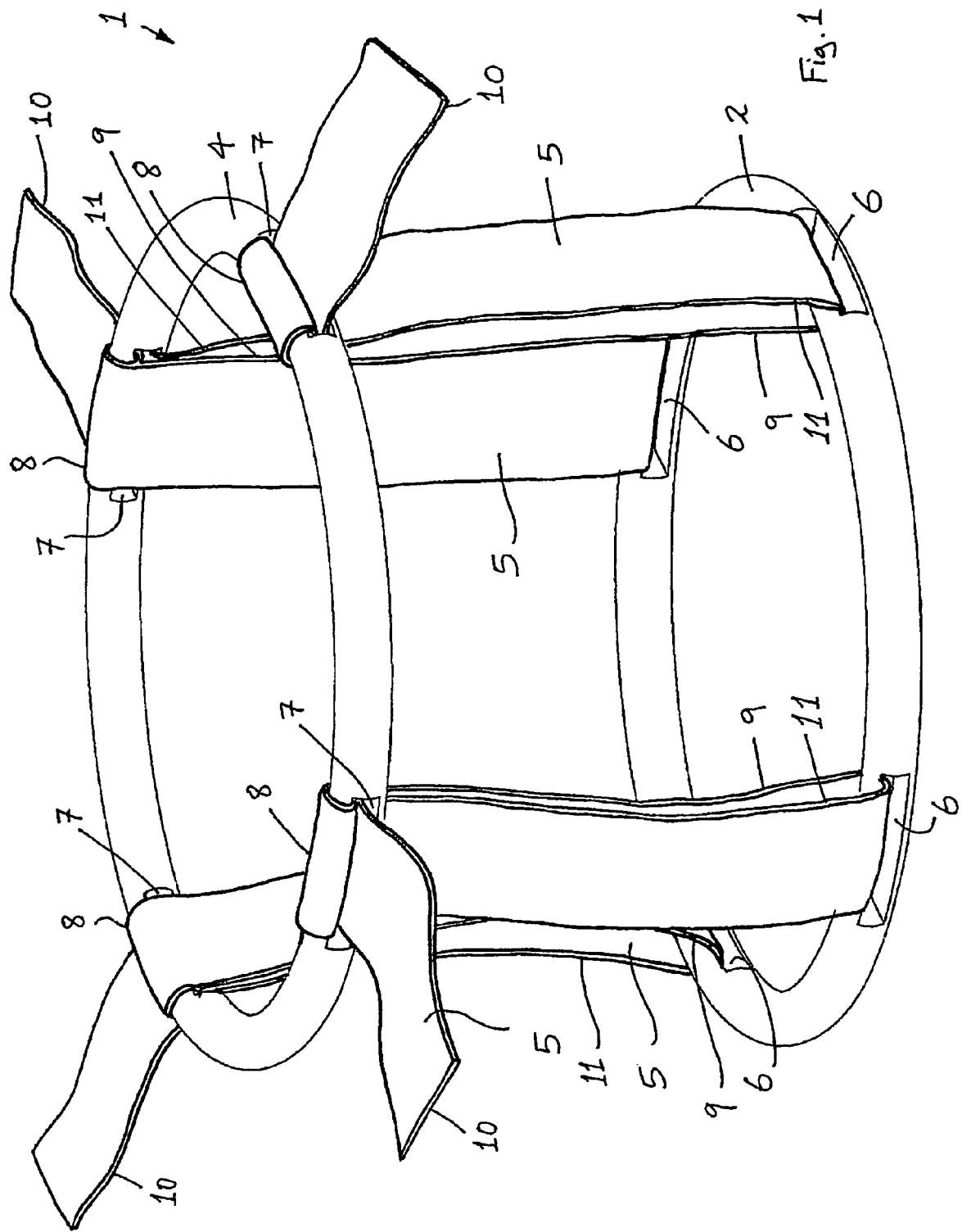
FIG. 1 is a perspective view of a wound retractor device according to the invention.
Figure 2:
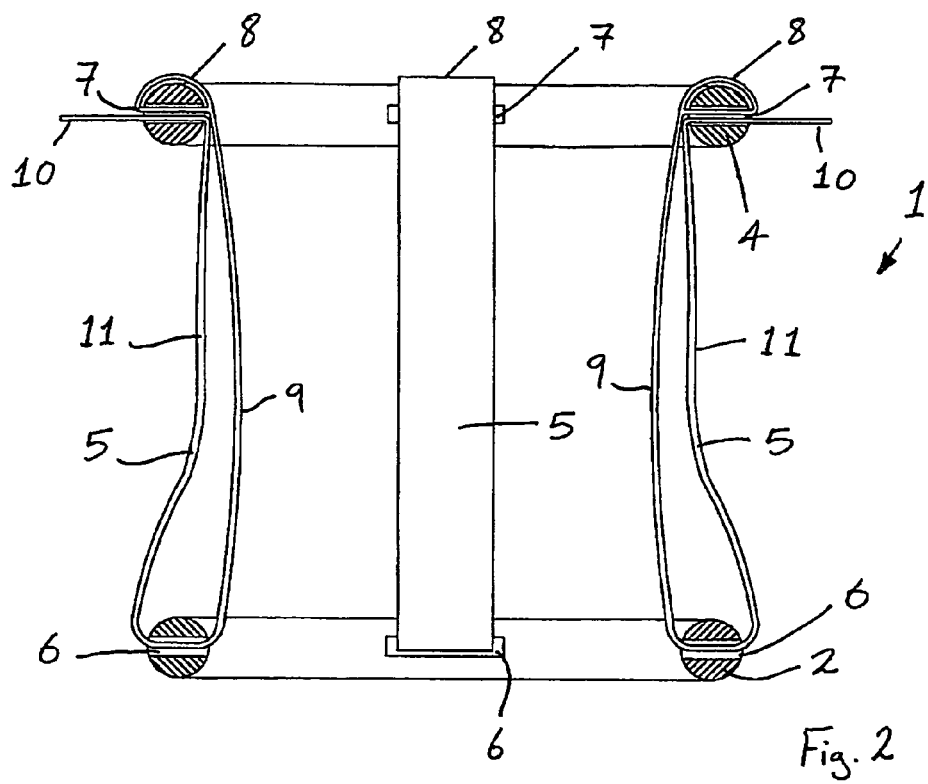
FIG. 2 is a cross-sectional, side view of the device of FIG. 1.
Figure 3:
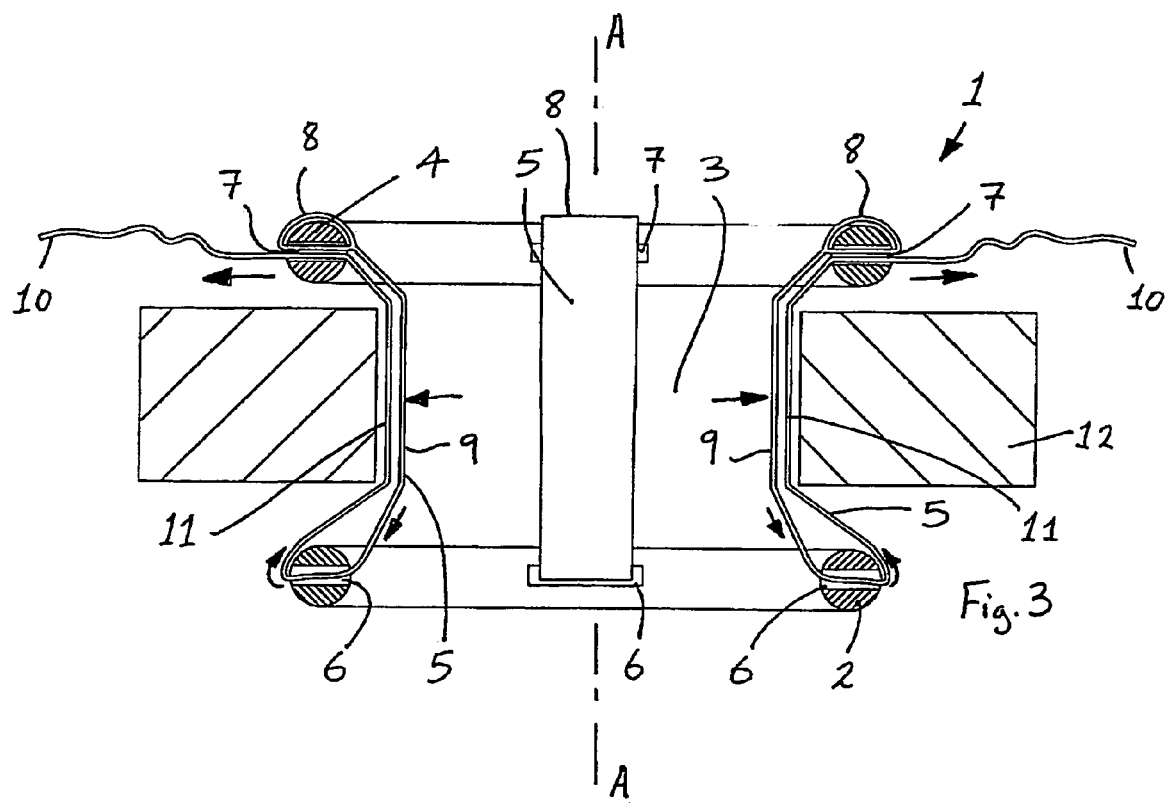
FIG. 3 is a cross-sectional, side view of the device of FIG. 1, in use.

Referring to the drawings, and initially to FIGS. 1 to 3 thereof, there is illustrated a wound retractor device 1 according to the invention. The device 1 comprises a distal ring member 2 for insertion into a wound opening 3, a proximal ring member 4 for location externally of the wound opening 3, and a connecting member extending between the proximal ring member 4 and the distal ring member 2. In this case the connecting member is provided in the form of four separate strap members 5 which are axially movable relative to the distal ring member 2 and relative to the proximal ring member 4. As illustrated in FIG. 1, the distal ring member 2 and the proximal ring member 4 are substantially circular.

The distal ring member 2 comprises four slots 6, with each strap member 5 positioned extending though a slot 6 (FIG. 1). Each strap member 5 is movable relative to the distal member 2 by sliding of the strap member 5 through the slot 6. The slots 6 thus act as passageways through which the strap members 5 may extend, and in this manner the slots 6 guide movement of the strap members 5 relative to the distal ring member 2. As illustrated in FIGS. 2 and 3, the longitudinal axis of each slot 6 is substantially perpendicular to a longitudinal axis A-A of the wound opening 3.

The proximal ring member 4 also comprises four slots 7 with each strap member 5 positioned extending through a slot 7 (FIG. 1). Each strap member 5 is movable relative to the proximal member 4 by sliding of the strap member 5 through the slot 7. The slots 7 thus act as passageways through which the strap members 5 may extend, and in this manner the slots 7 guide movement of the strap members 5 relative to the proximal ring member 4. As illustrated in FIGS. 2 and 3, the longitudinal axis of each slot 7 is substantially perpendicular to the longitudinal axis A-A of the wound opening 3.

A first end 8 of each strap member 5 is fixedly attached to the proximal ring member 4, with each strap member 5 extending between the distal ring member 2 and proximal ring member 4 in a double layer. In particular, each strap member 5 extends from the first end 8 fixed to the proximal ring member 4 distally towards the distal ring member 2 in a first layer 9. At the distal ring member 2, each strap member 5 is looped through the slot 6. Each strap member 5 then extends from the distal rig member 2 proximally to a second end 10 of the strap member 5 in a second layer 11. As illustrated in FIGS. 2 and 3, the second layer 11 is located radially outwardly of the first layer 9, with the second layer 11 bearing against the sides of the wound opening 3 (FIG. 3).

The four strap members 5 are evenly spaced around the circumference of the distal ring member 2 and around the circumference of the proximal ring member 4. In this manner, an even retracting force is applied to the sides of the wound opening 3.

In use, the distal ring member 2 is inserted into the wound opening 3, and the proximal ring member 4 is located externally of the wound opening 3. The second end 10 of each strap member 5 is then gripped, and a pulling force is exerted on each second end 10 to pull each second end 10 laterally, radially outwardly parallel to the longitudinal axis of the slots 7 away from the proximal ring member 4, as illustrated in FIG. 3. This pulling action causes each strap member 5 to be pulled axially through the slot 6 in the distal ring member 2 in a sliding manner and through the slot 7 in the proximal ring member 4 in a sliding manner, as indicated by the arrows in FIG. 3.

As a result the length of each strap member 5 which is located between the distal ring member 2 and the proximal ring member 4 is shortened, and initially the distal ring member 2 is drawn upwardly towards the proximal ring member 4. When the distal ring member 4 reaches the inner surfaces of the peritoneum 12, further pulling of each strap member 5 will cause shortening of the length of each strap member 5 which is located between the distal ring member 2 and the proximal ring member 4 by retracting laterally the sides of the wound opening 3 (FIG. 3). After lateral retraction of the sides of the wound opening 3, the second end 10 of each strap member 5 may be released.

As the strap members 5 are pulled and the wound opening 3 is retracted, the slots 6 guide movement of the strap members 5 relative to the distal ring member 2, and the slots 7 guide movement of the strap members 5 relative to the proximal ring member 4. In this way, the slots 6, 7 provide the surgeon with enhanced control of the strap members 5.

The wound retractor device 1 is self-locking. Thus, when the pulling force is released, the strap members 5 remain locked in position with the wound opening 3 retracted (FIG. 3).

Figure 4:
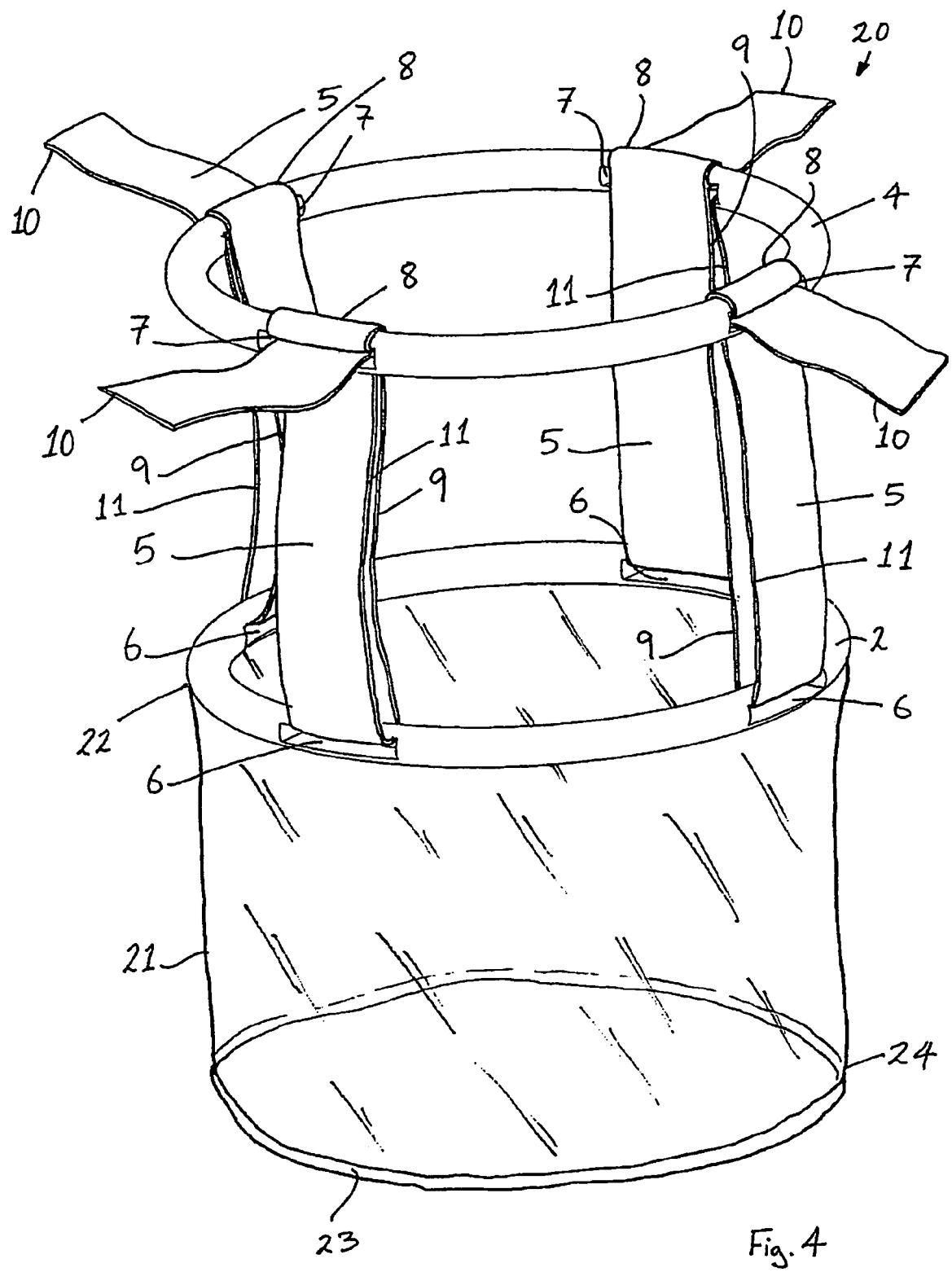

FIGS. 4 to 6 illustrate another wound retractor device 20 according to the invention, which is similar to the device 1 of FIGS. 1 to 3, and similar elements in FIGS. 4 to 6 are assigned the same reference numerals.

In this case, the device 20 comprises a cylindrical film sleeve member 21 for lining the retracted wound opening 3 to protect the retracted wound opening 3. A first end 22 of the sleeve member 21 is mounted to the distal ring member 2 by fixedly attaching the first end 22 to the distal ring member 2. A ring 23 is provided at a second end 24 of the sleeve member 21.

In use, the distal ring member 2 and the sleeve member 21 are together inserted into the wound opening 3. The ring 23 is then gripped and pulled back out of the wound opening 3, and located externally of the wound opening 3 between the proximal ring member 4 and the peritoneum 12, as illustrated in FIG. 6. In this manner, the sleeve member 21 is retrieved from within the wound opening 3 and located between the strap members 5 and the sides of the wound opening 3. Retraction of the wound opening 3 may then be performed as described previously with reference to FIGS. 1 to 3. The sleeve member 21 thus acts to line the retracted wound opening 3 to protect the retracted wound opening 3, as illustrated in FIG. 6.

It will be appreciated that the sleeve member 21 may alternatively be provided disconnected from the distal ring member 2.

Figure 7:
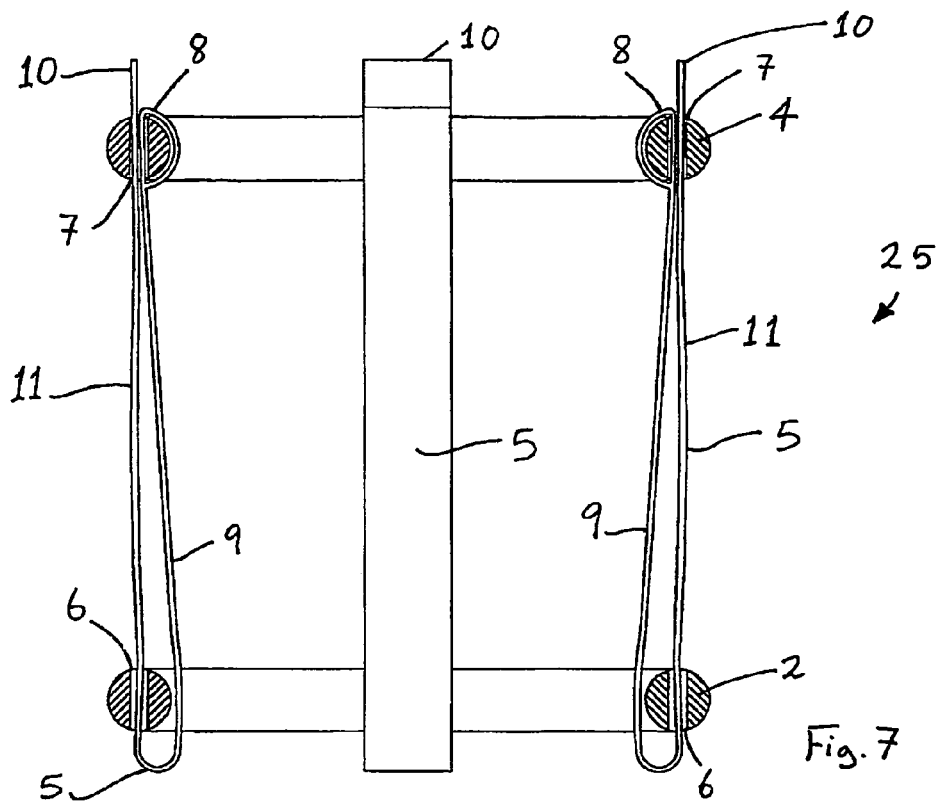
FIGS. 7 and 8 are views similar to FIGS. 2 and 3 of a further wound retractor device according to the invention.
Figure 8:
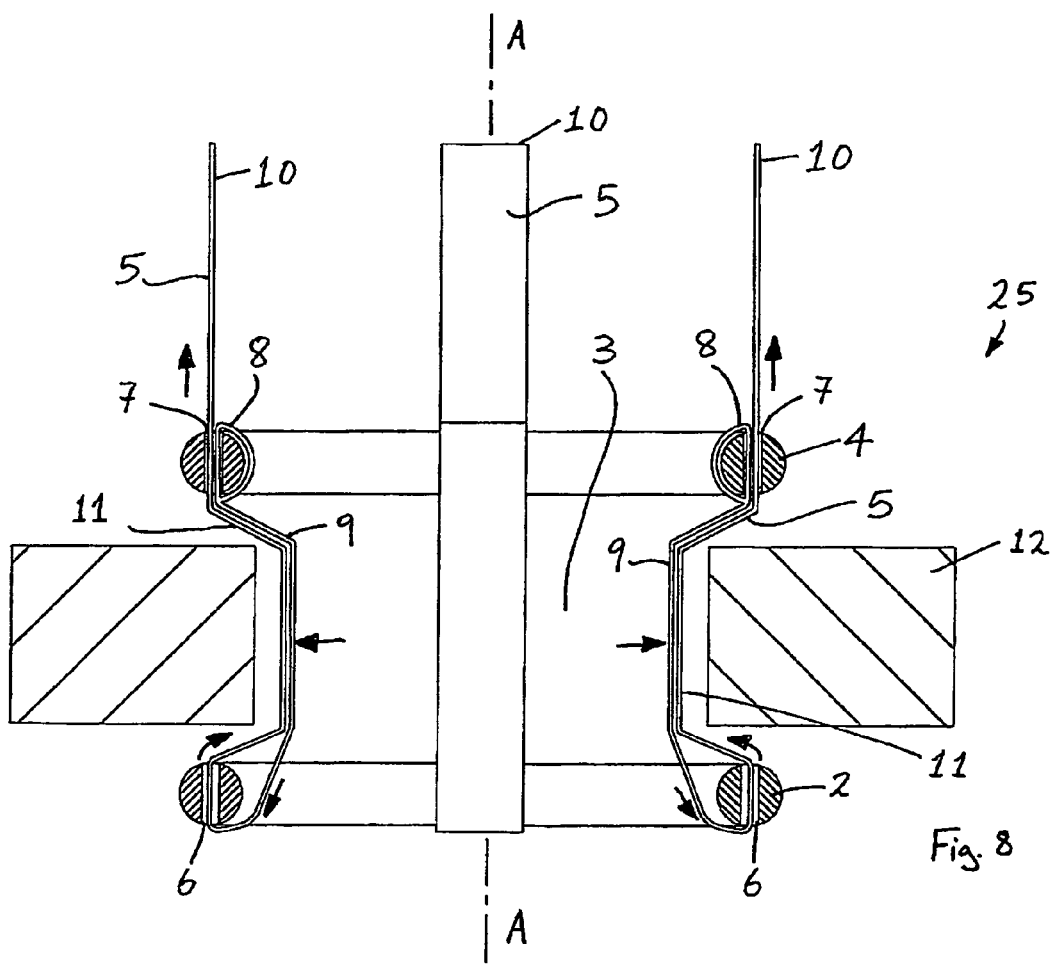

In FIGS. 7 and 8 there is illustrated a further wound retractor device 25 according to the invention, which is similar to the device 1 of FIGS. 1 and 3, and similar elements in FIGS. 7 and 8 are assigned the same reference numerals.

In this case, the longitudinal axis of each slot 6 and the longitudinal axis of each slot 7 are substantially parallel to the longitudinal axis A-A of the wound opening 3. To retract the wound opening 3, the strap members 5 are pulled upwards parallel to the longitudinal axis of the slots 7 away from the proximal ring member 4, as illustrated in FIG. 8.

FIGS. 9 and 10 illustrate another wound retractor device 30 according to the invention, which is similar to the device 1 of FIGS. 1 to 3, and similar elements in FIGS. 9 and 10 are assigned the same reference numerals.

In this case, the longitudinal axis of the each slot 7 subtends an acute angle, for example a 45° angle, with the longitudinal axis A-A of the wound opening 3. To retract the wound opening 3, the strap members 5 are pulled upwards parallel to the longitudinal axis of the slots 7 away from the proximal ring member 4, as illustrated in FIG. 10.

It will be appreciated that the longitudinal axis of each slot 6 and/or the longitudinal axis of each slot 7 may be arranged at any suitable angle relative to the longitudinal axis A-A of the wound opening 3.

Figure 11:
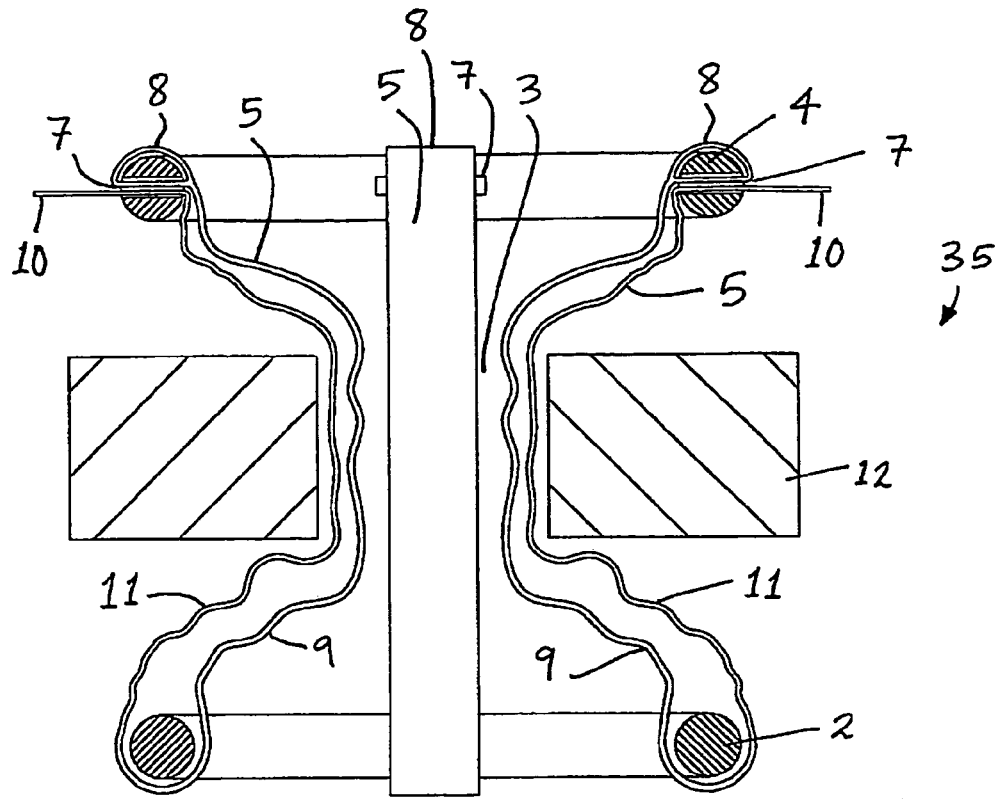
FIGS. 11 and 12 are cross-sectional, side views of a further wound retractor device according to the invention, in use.
Figure 12:
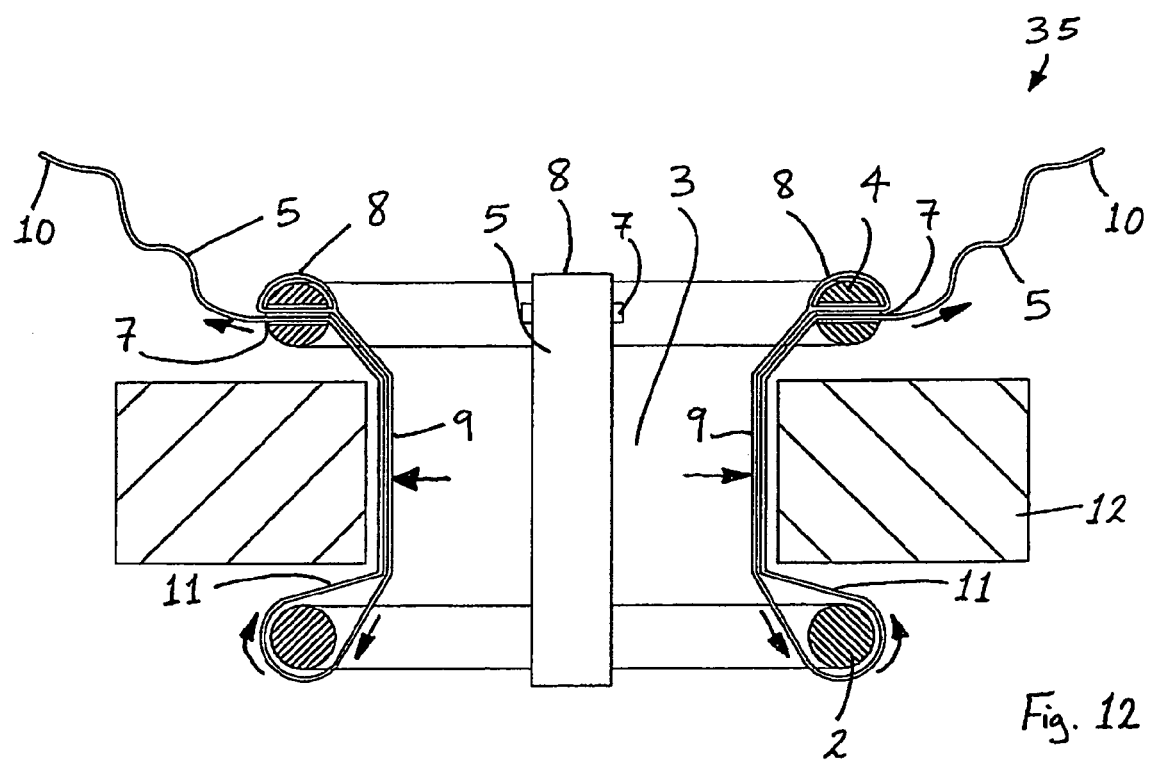

Referring to FIGS. 11 and 12 there is illustrated another wound retractor device 35 according to the invention, which is similar to the device 1 of FIGS. 1 to 3, and similar elements in FIGS. 11 and 12 are assigned the same reference numerals.

In this case, there are no slots provided in the distal ring member 2. Instead each strap member 5 is looped around the entire distal ring member 2. In this manner the distal ring member 2 is associated with the strap members 5.

Figure 13:
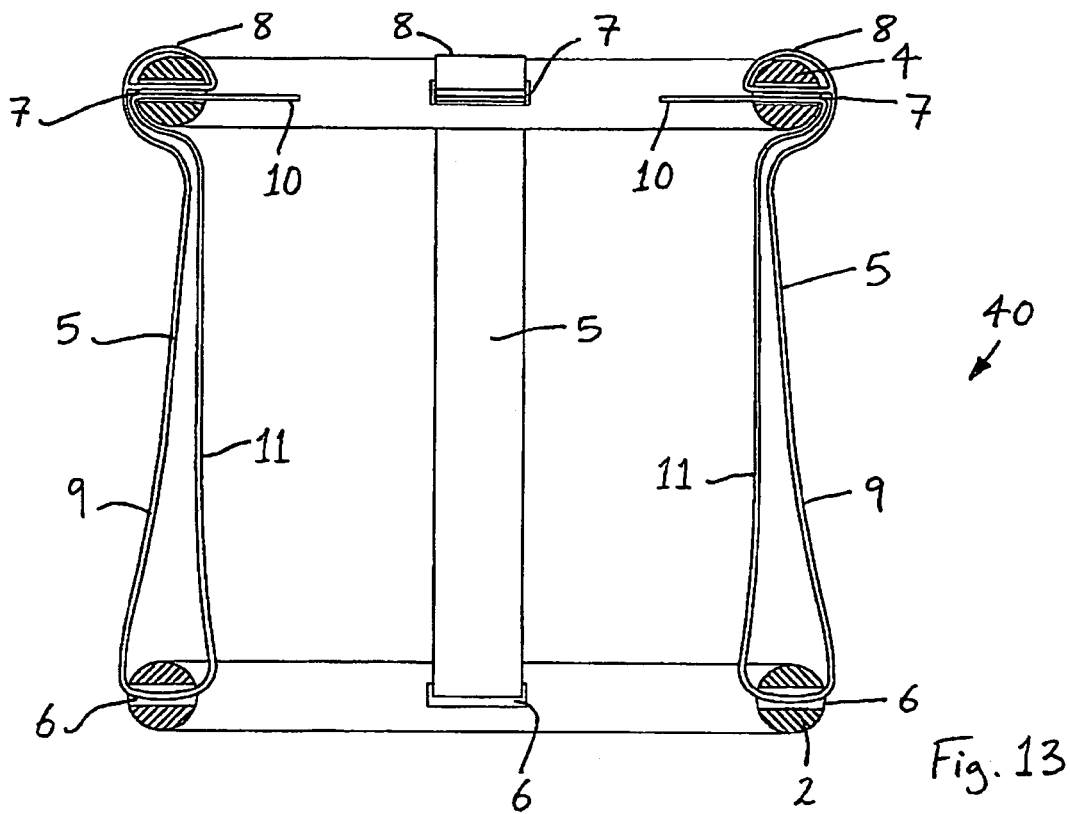
FIGS. 13 and 14 are views similar to FIGS. 2 and 3 of another wound retractor device according to the invention.
Figure 14:
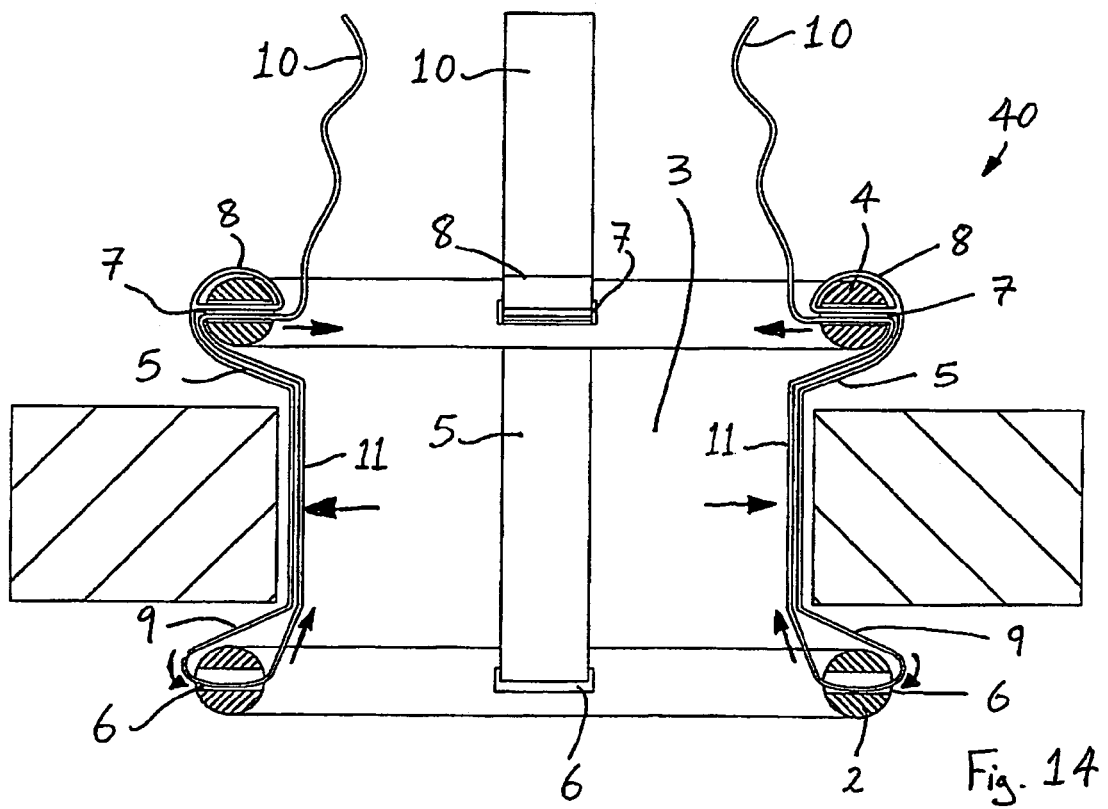

In FIGS. 13 and 14, there is illustrated another wound retractor device 40 according to the invention, which is similar to the device 1 of FIGS. 1 to 3, and similar elements in FIGS. 13 and 14 are assigned the same reference numerals.

In this case, the second layer 11 of each strap member 5 is located radially inwardly of the first layer 9, with the first layer 9 bearing against the sides of the wound opening 3 (FIG. 14). To retract the wound opening 3, the strap members 5 are pulled laterally radially inwardly parallel to the longitudinal axis of the slots 7 away from the proximal ring member 4, as illustrated in FIG. 14.

Figure 15:
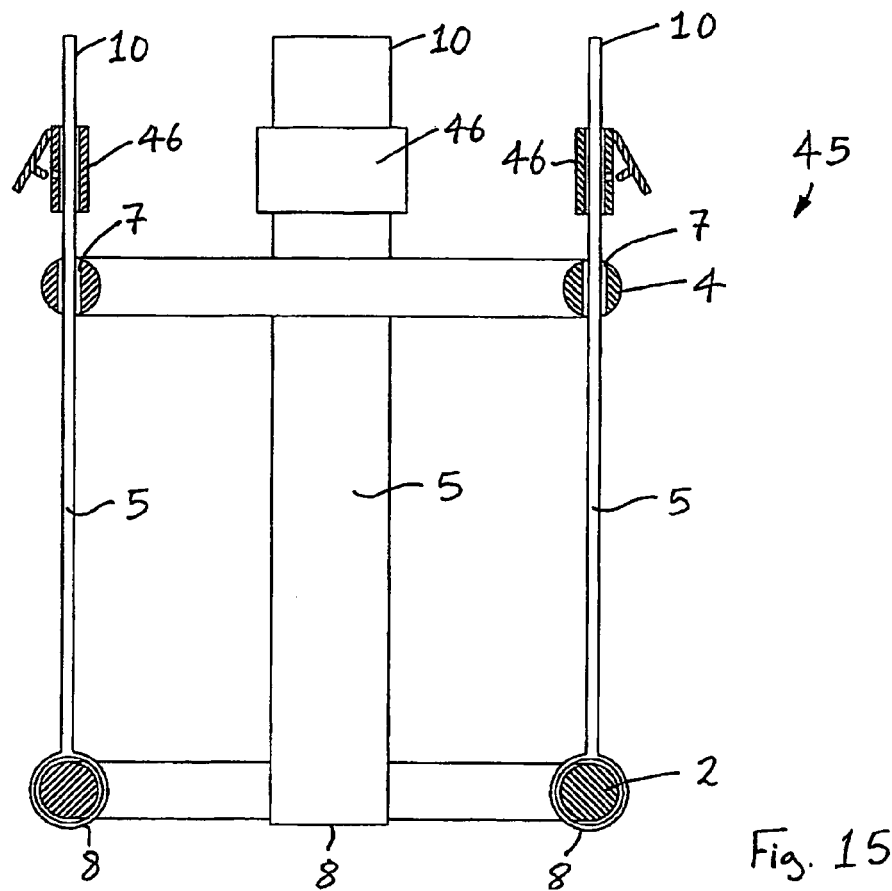
FIGS. 15 and 16 are views similar to FIGS. 2 and 3 of another wound retractor device according to the invention.
Figure 16:
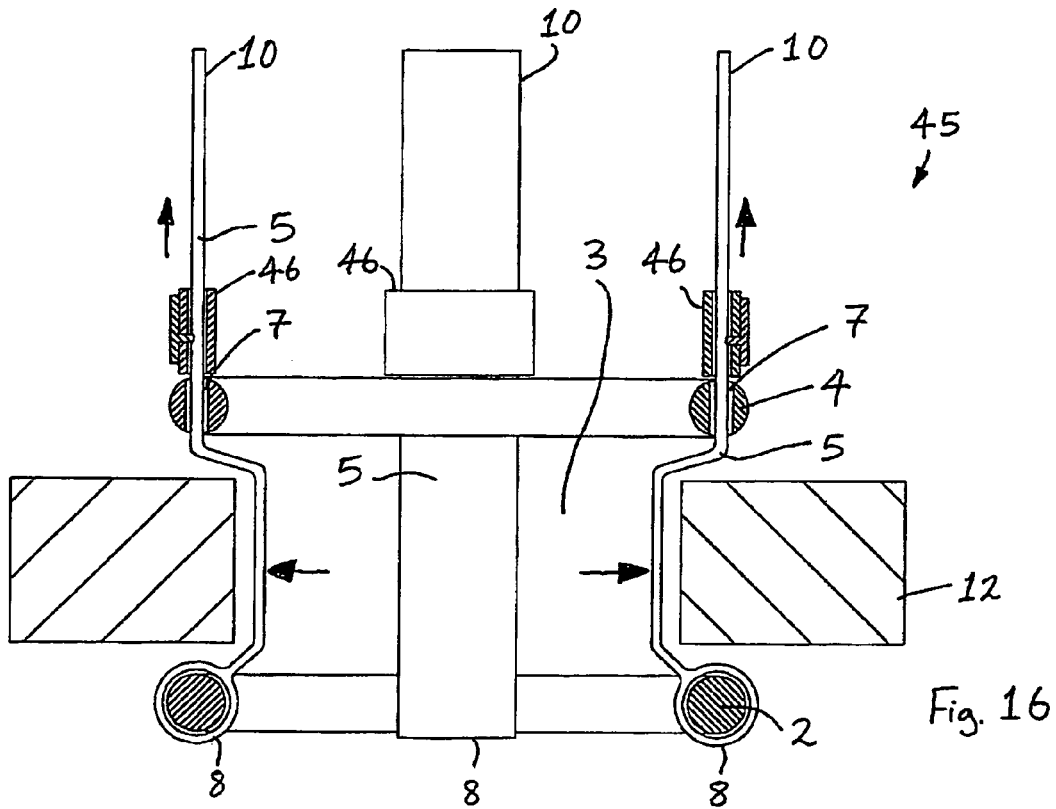

In FIGS. 15 and 16, there is illustrated a further wound retractor device 45 according to the invention.

In this case, there are no slots provided in the distal ring member 2, and the first end 8 of each strap member 5 is fixedly attached to the distal ring member 2. Each strap member 5 extends between the distal ring member 2 and the proximal ring member 4 in a single layer.

In addition, the wound retractor device 45 is not self-locking. Instead the device 45 comprises four clamps 46. Each clamp 46 is releasably fixable to a strap member 5 at a desired location along the strap member 5. When the wound opening 3 has been retracted, each clamp 46 is fixed to a strap member 5 at a location engaging against the proximal ring member 4 (FIG. 16). In this manner, the strap members 5 are releasably locked in position relative to the proximal ring member 4, and the wound opening 3 is thus releasably locked in the retracted configuration.

Figure 17:
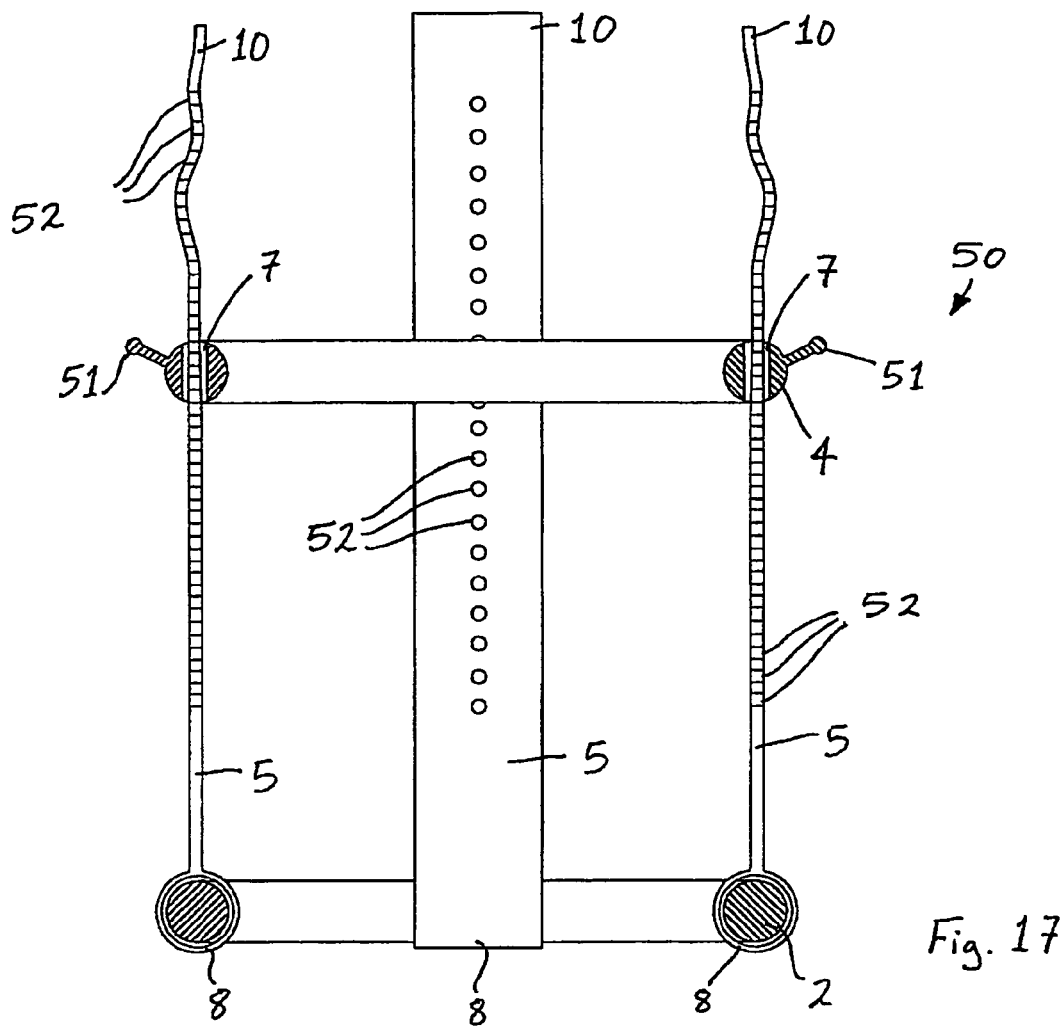
FIGS. 17 and 18 are views similar to FIGS. 2 and 3 of a further wound retractor device according to the invention.
Figure 18:
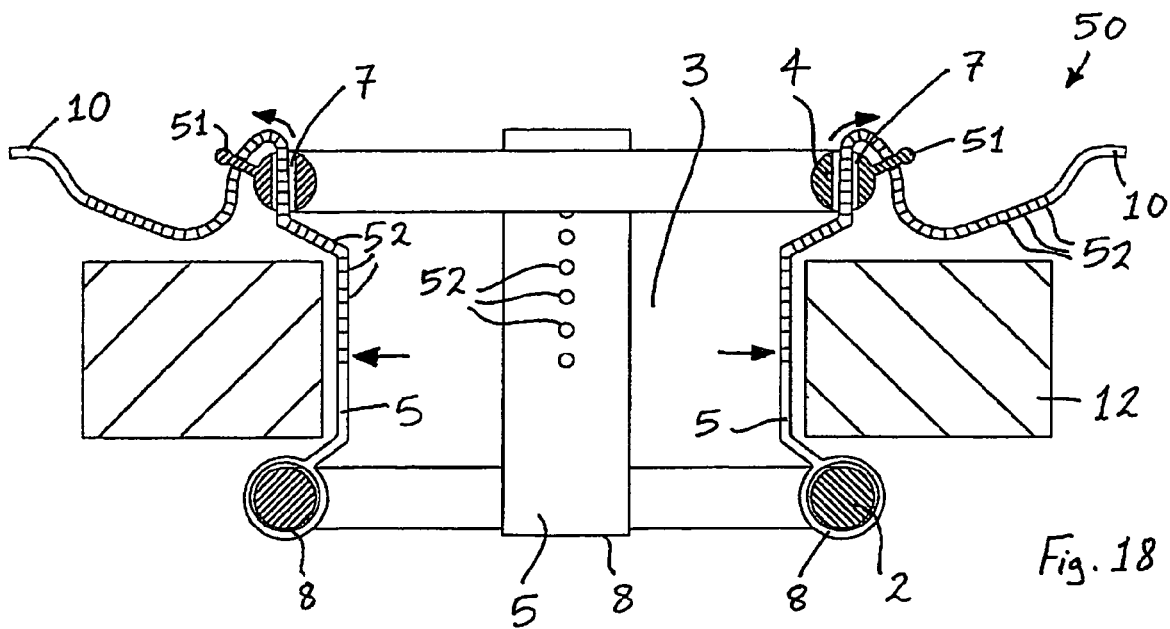

Referring to FIGS. 17 and 18 there is illustrated another wound retractor device 50 according to the invention, which is similar to the device 45 of FIGS. 15 and 16, and similar elements in FIGS. 17 and 18 are assigned the same reference numerals.

In this case, the proximal ring member 4 comprises four male protrusions 51, and each strap member 5 comprises a plurality of female recess openings 52. Each male protrusion 51 is inserted into one of the openings 52 of a strap member 5 for co-operative engagement of the male protrusion 51 with the opening 52 (FIG. 18). In this manner, the strap members 5 are locked in position relative to the proximal ring member 4, and the wound opening 3 is thus locked in the retracted configuration.

FIG. 19 illustrates another wound retractor device 55 according to the invention, which is similar to the device 35 of FIGS. 11 and 12, and similar elements in FIGS. 19 to 21 are assigned the same reference numerals.

In this case, the device 55 comprises two strap members 5, and no slots are provided in the proximal ring member 4.

It will be appreciated that any suitable number of one or more strap members 5 may be provided in the wound retractor device according to the invention to achieve the desired retraction of the wound opening 3.

In FIGS. 20 to 21(*a*) there is illustrated a further wound retractor device 155 according to the invention, which is similar to the device 55 of FIG. 19, and similar elements in FIGS. 20 to 21(*a*) are assigned the same reference numerals.

In this case the connecting member, which extends between the proximal ring member 4 and the distal ring member 2, is provided in the form of a sleeve member 156 and two strap members 5. The two strap members 5 extend from an end of the sleeve member 156 in the same direction.

The first end 8 of the sleeve member 156 is fixedly attached to the proximal ring member 4, and extends distally towards the distal ring member 2 in the first layer 9. At the distal ring member 2, the sleeve member 156 is looped around the entire distal ring member 156. The two strap members 5 are attached to an end of the sleeve member 5, and extend from the end of the sleeve member 156 proximally to the second end 10 in the second layer 11.

As illustrated in FIG. 20, the two strap members 5 are attached together, in this case with the sleeve member 156 providing the means of attachment.

The circumferential dimension of the sleeve member 156 is substantially equal to the sum of the circumferential dimension of the two strap members 5, as illustrated in FIG. 20.

The wound retractor device 155 is self-locking to maintain the wound opening 3 laterally retracted.

To maintain the wound opening 3 in the retracted configuration the second 10 of each strap member 5 does not have to pass through a slot in the proximal ring member 4, or to be hooked onto the proximal ring member 4, or in any other way to be engaged against the proximal ring member 4. The wound retractor device 155 is self-locking, even when the second ends 10 of the strap members 5 do not engage against the proximal ring member 4.

After lateral retraction of the sides of the wound opening 3, the portion of the second layer 11 of each strap member 5 which is external of the wound opening 3 is redundant. This external portion of each strap member 5 does not contribute to maintaining the wound opening 3 retracted, and may therefore be removed if desired, for example by cutting this external portion.

The second ends 10 of the strap members 5 may be moved in a direction substantially parallel to the longitudinal axis A-A of the wound opening 3 to retract laterally the sides of the wound opening 3, as illustrated in FIGS. 20 and 21.

Alternatively the second ends 10 of the strap members 5 may be moved in a lateral direction to retract laterally the sides of the wound opening 3, as illustrated in FIG. 21(*a*). In this case, the second ends 10 are moved in a direction substantially perpendicular to the longitudinal axis A-A of the wound opening 3.

Referring to FIG. 22, there is illustrated a further wound retractor device 56 according to the invention, which is similar to the device 55 of FIG. 19, and similar elements in FIG. 22 are assigned the same reference numerals.

In this case, the distal ring member 2 and the proximal ring member 4 are substantially square-shaped. The square shape acts to prevent bunching of, in particular, the distal ring member 2.

It will be appreciated that the distal ring member 2 and/or the proximal ring member 4 may be provided in a variety of different shapes.

It will further be appreciated that hinging means may be provided on the distal ring member 2 to facilitate temporary collapsing of the distal ring member 2 to a lower-profile configuration for ease of insertion into the wound opening 3.

The invention is not limited to the embodiments hereinbefore described, with reference to the accompanying drawings, which may be varied in construction and detail.

The invention claimed is:

1. A wound retractor device comprising:
   a distal member for insertion into a wound opening;
   a proximal member for location externally of the wound opening; and
   a plurality of straps,
      each strap extending from the proximal member to the distal member and from the distal member to the proximal member to form a double layer configuration,
      each strap being movably connected to the distal member, and
      each strap being movable relative to the proximal member to shorten the length of the strap located between the distal member and the proximal member to retract laterally the sides of the wound opening.

2. A device as claimed in claim 1 further including a protector sleeve extending at least between the proximal member and the distal member.

3. A device as claimed in claim 2 wherein the protector sleeve includes a first end fixedly connected to the distal member and a second end configured for location externally of the wound opening.

4. A device as claimed in claim 3 wherein the plurality of straps are located radially within the protector sleeve when the device is retracting the wound opening.

5. A device as claimed in claim 1 wherein each strap includes a first end fixedly connected to the proximal member and a second end movably connected to the proximal member.

6. A device as claimed in claim 5 wherein each strap extends from the first end distally to the distal member in a first layer, and extends from the distal member proximally to the second end in a second layer, the second layer being located radially outwardly of the first layer.

7. A device as claimed in claim 5 wherein each strap extends through a slot formed in the proximal member.

8. A device as claimed in claim 7 wherein the slot extends generally perpendicular to a longitudinal axis of the device.

9. A device as claimed in claim 7 wherein each strap extends through a slot formed in the distal member.

10. A device as claimed in claim 9 wherein the slot formed in the distal member extends generally perpendicular to a longitudinal axis of the device.

11. A device as claimed in claim 1 wherein each strap is configured to self-lock in position relative to the proximal member.

12. A method of retracting a wound opening with a wound retractor device comprising a distal member, a proximal member, and a plurality of straps, each strap extending from the proximal member to the distal member and from the distal member to the proximal member to form a double layer configuration, the method comprising:
    inserting the distal member into the wound opening, and locating the proximal member externally of the wound opening; and
    moving each strap relative to the proximal member and the distal member to shorten the length of the strap located between the distal member and the proximal member to retract laterally the sides of the wound opening.

13. A method as claimed in claim 12 wherein at least part of the strap is slidably moved relative to the proximal member.

14. A method as claimed in claim 12 further including gripping at least part of the strap and exerting a force on the strap to move at least part of the strap relative to the proximal member.

15. A method as claimed in claim 12 further including guiding movement of the strap relative to the proximal member by a slot formed in the proximal member.

16. A method as claimed in claim 15 further including guiding movement of the strap relative the distal member by a slot formed in the distal member.

17. A method as claimed in claim 12 wherein the plurality of straps individually self-lock in position relative to the proximal member.

18. A method as claimed in claim 12 further including protecting the retracted opening with a protector sleeve located between the plurality of straps and the sides of the wound opening.

19. A method as claimed in claim 18 wherein the protector sleeve is inserted into the wound opening with the distal member.

20. A wound retractor device comprising:
    a distal ring for insertion into a wound opening;
    a proximal ring for location externally of the wound opening; and
    a plurality of straps,
        each strap including a first end and a second end, the first end being fixedly connected to the proximal ring and the second end being slidably connected to the proximal ring,
        each strap extending from the proximal ring to the distal ring and from the distal ring to the proximal ring to form a double layer configuration,
        each strap being slidably connected to the distal ring, and
        sliding a strap relative to the proximal ring shortens the length of the strap located between the distal ring and the proximal ring to retract laterally the sides of the wound opening.

21. A device as claimed in claim 20 further including a protector sleeve extending at least between the proximal ring and the distal ring.

22. A device as claimed in claim 21 wherein the protector sleeve includes a first end fixedly connected to the distal ring and a second end configured for location externally of the wound opening.

23. A device as claimed in claim 22 wherein the plurality of straps are located radially within the protector sleeve when the device is retracting the wound opening.

24. A device as claimed in claim 20 wherein each strap extends from the first end distally to the distal ring in a first layer, and extends from the distal ring proximally to the second end in a second layer, the second layer being located radially outwardly of the first layer.

25. A device as claimed in claim 20 wherein each strap extends through a slot formed in the proximal ring.

26. A device as claimed in claim 25 wherein the slot extends generally perpendicular to a longitudinal axis of the device.

27. A device as claimed in claim 25 wherein each strap extends through a slot formed in the distal ring.

28. A device as claimed in claim 27 wherein the slot formed in the distal ring extends generally perpendicular to a longitudinal axis of the device.

29. A device as claimed in claim 20 wherein each strap is configured to self-lock in position relative to the proximal ring.

* * * * *